United States Patent
McCrary et al.

(10) Patent No.: US 8,029,497 B2
(45) Date of Patent: Oct. 4, 2011

(54) ONE-PIECE FLUID SUCTIONING DEVICE

(75) Inventors: Craig R. McCrary, Valencia, CA (US);
Thomas R. Thornbury, Los Angeles, CA (US); Arnold M. Heyman, Los Angeles, CA (US)

(73) Assignee: Neotech Products, Inc., Valencia, CA (US)

( * ) Notice: Subject to any disclaimer, the term of this patent is extended or adjusted under 35 U.S.C. 154(b) by 599 days.

(21) Appl. No.: 12/217,593

(22) Filed: Jul. 8, 2008

(65) Prior Publication Data

US 2010/0010435 A1    Jan. 14, 2010

(51) Int. Cl.
*A61M 1/00*    (2006.01)

(52) U.S. Cl. ........ 604/540; 604/264; 604/268; 604/275; 604/276; 604/533; 604/534; 604/535; 604/537; 604/538; 604/290; 604/310; 604/313; 604/316; 604/543; 604/320; 604/323; 604/30; 604/36; 604/118; 604/129; 604/164.02; 604/164.04; 604/164.07; 604/165.01; 604/165.02; 604/167.03; 604/167.04; 604/167.06; 604/234

(58) Field of Classification Search .................. 604/540, 604/264, 268, 275, 276, 533, 534, 535, 537, 604/538, 290, 310, 313, 316, 543, 320, 323, 604/30, 36, 118, 129, 164.02, 164.04, 164.07, 604/165.01, 165.02, 167.03, 167.04, 167.06, 243

See application file for complete search history.

(56) References Cited

U.S. PATENT DOCUMENTS

| | | | |
|---|---|---|---|
| 3,319,628 A | 5/1967 | Halligan | |
| 4,266,814 A | 5/1981 | Gallagher | |
| 4,729,765 A | 3/1988 | Eckels et al. | |
| 5,496,268 A | 3/1996 | Peria | |
| 5,507,535 A | 4/1996 | McKamey et al. | |
| 5,913,852 A * | 6/1999 | Magram | 604/540 |
| D449,378 S | 10/2001 | Rogone et al. | |
| 6,958,050 B1 | 10/2005 | Choski et al. | |
| 2009/0043286 A1* | 2/2009 | McCrary et al. | 604/541 |

* cited by examiner

*Primary Examiner* — Melanie Hand
*Assistant Examiner* — Ginger T Chapman
(74) *Attorney, Agent, or Firm* — William W. Haefliger

(57) ABSTRACT

A mucous suction device, comprising in combination, a longitudinally elongated, generally tubular, one-piece plastic body, the body having an axially elongated tapered, first portion extending toward an inlet proximate one end of the body, the body having an axially elongated second portion extending toward an outlet proximate an opposite end of the body, radially outwardly extending annular retention rings in said body second portion, said rings having sharp annular peripheries and said rings being axially resiliently flexible and axially spaced apart, and there being body side porting between said body first and second portions, said side porting being manually controllable to control suction exertion.

18 Claims, 2 Drawing Sheets

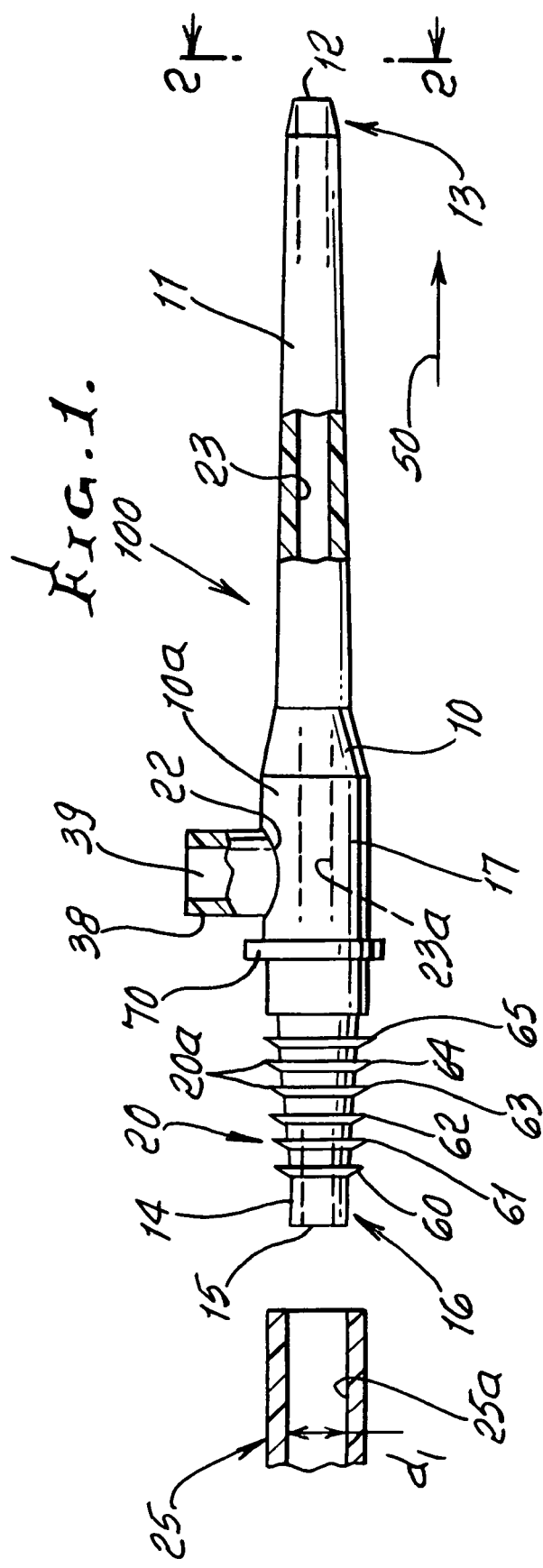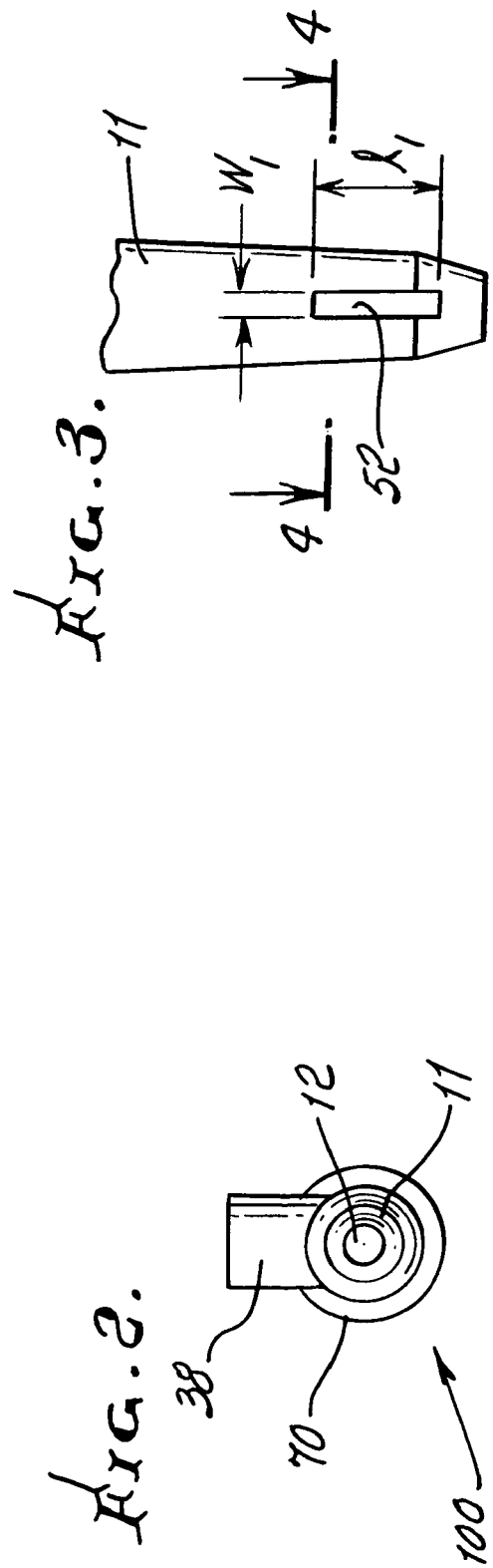

ONE-PIECE FLUID SUCTIONING DEVICE

BACKGROUND OF THE INVENTION

This invention relates generally to medical suctioning or aspiration devices and methods, and more particularly to an improved device and method characterized by increased overall utility, as well as ease and effectiveness of use and operation.

There is need for improvements in devices of the type referred to above. Also, there is need for devices and methods embodying the novel and unusual features of construction, modes of operation and results found in the device and methods of use embodied in the present invention. This invention improves upon the devices of U.S. Pat. Nos. 6,958,050 and 4,729,765.

SUMMARY OF THE INVENTION

It is a major object of the invention to provide an improved suctioning device and method of its use, as referred to. Basically, the device comprises:

a) a longitudinally elongated, generally tubular, one-piece plastic body, b) the body having an axially elongated tapered, first portion extending toward an inlet proximate one end of the body, c) the body having an axially elongated second portion extending toward an outlet proximate an opposite end of the body, d) radially outwardly extending annular retention rings on said body second portion, said rings having sharp annular peripheries and the rings being axially resiliently flexible and axially spaced apart, e) and there being body side porting between said body first and second portions, the side porting being manually controllable to control suction exertion.

Another object is to provide a body bore that has constant, i.e. unstepped, diameter between the inlet and outlet, and to provide the rings to have axially flexible molded plastic peripheries for establishing annular seals in response to axial reception of a connector tubing bore onto and over the body second portion. In this regard, the connector tubing that fits over the rings has a bore with interference engagement with at least three of said rings, whereby those three rings are flexed axially at their peripheries, thereby to establish annular seals. The rings are typically axially spaced apart on a body conical surface whereby each ring is independently axially flexible, the rings closer to the body first portion being flexed to greater extent than other rings, to establish greater local retention to the connector tubing. Accordingly, the degree of such retention can be more accurately controlled by and in response to the degree of push-on advancement of that tubing relative to the rings.

A further object is to provide the rings to have front and back flanks, and wherein for each pair of rings, the successive back flank of one ring of the pair is everywhere spaced axially from the front flank of the other ring of the pair whereby each ring is independently axially flexible. Typically, the back flanks extend at angles α relative to the axially elongated direction and the front flanks extend at angles β relative to the axially elongated direction, and wherein β>α and α>45°, and said body second portion has a conical surface from which the rings project outwardly.

Yet another object is to provide a body side wall inlet to have elongated length $l_l$ in the length direction of the tubing elongated first portion, and has narrowed width $w_l$ along said length $l_l$, and wherein $l_l \gg w_l$.

These and other objects and advantages of the invention, as well as the details of an illustrative embodiment, will be more fully understood from the following specification and drawings, in which:

DRAWING DESCRIPTION

FIG. 1 is a side elevation view of a preferred device incorporating the invention;

FIG. 2 is an end view taken on lines 2-2 of FIG. 1;

FIG. 3 is a top plan view taken on a modified device stem, showing a side inlet;

DETAILED DESCRIPTION

Figure 4:
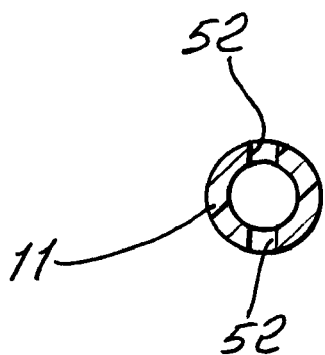
FIG. 4 is a section taken on lines 4-4 of FIG. 3.

The drawings show the improved and preferred multipurpose medical suctioning device 100, which is of one-piece, integrally molded synthetic resinous (plastic) composition. It includes:

a) a longitudinally and axially elongated, generally tubular, one-piece plastic body 10, b) the body 10 having an axially elongated, tapered, first portion 11 extending toward an inlet 12 proximate an end 13 of the body, to receive fluid being suctioned, c) the body 10 having an axially elongated second portion 14, extending from an outlet 15 proximate an opposite end 16 of the body, and toward a body mid-portion 17, d) radially outwardly extending annular retention and sealing rings 20 on the body second portion 14, the thin rings having narrow and sharp annular peripheries 20a, and being axially stiffly resilient, and axially spaced apart, e) and the body having side porting 22 at the mid porting 17, and being manually or finger controllable to control suction exertion.

It will be seen that the body preferably has a continuous bore 23 extending between the body opposite ends 13 and 16, the bore having constant or substantially constant, unstepped diameter along the entire body length between such steps, whereby flow of suctional fluid is unimpeded, through the body and to connector tubing. Such tubing is shown at 25 in FIG. 1 before its push-on connection over rings 20, and also in FIG. 5 after such push-on connection.

Figure 5:
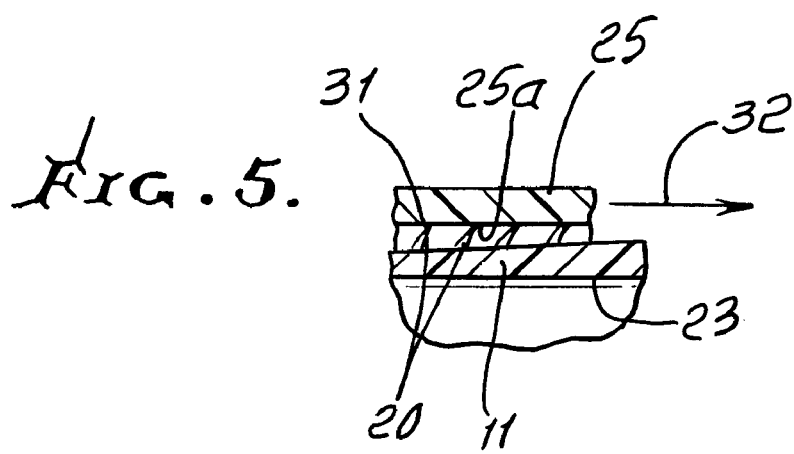
FIG. 5 is an enlarged fragmentary section, showing retention rings in the body and having peripheries engaging and being progressively and controllably flexed by engagement with the bore and connector tubing.

It will be noted that the rings are resiliently axially flexible, particularly at their peripheries 31, for establishing annular seals in response to axial reception, i.e. push-on, of the bore 25a of tubing 25 over the rings. The ring peripheries progressively increase in diameter, in the push-on direction 32, whereby the progressively forwardmost rings flex to greater progressive extent, for gripping the tubing bore, as seen in FIG. 5. Accordingly, the degree of gripping can be accurately controlled by the extent of push-on of the tubing, whereas, all or substantially all of the rings sub-tended by the connector tubing engage its bore to establish sealing at multiple locations, safe and full suctioning thereby being assured. The structure also accommodates tubing bore diameters that vary.

Figure 6:
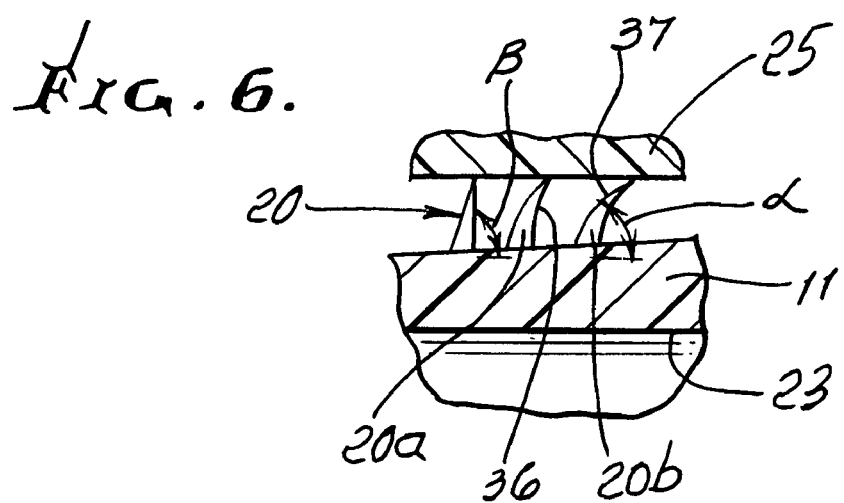
FIG. 6 is a still further enlarged section showing the angular relationships between ring front and rear flanks.

Note also in FIG. 6 that the rings have front flanks 36, and back flanks 37. For each pair of successive rings, as for example at 20a and 20b, the back flank 37 of ring 20b is everywhere spaced axially from the front flank 36 of ring 20a, whereby each ring is independently axially flexible, maintaining or enhancing the integrity of the sealing and anchoring (gripping) function and results, for differing connector bore diameters. As shown in FIG. 6, the bank flanks extend at angles α relative to the axially elongated direction and the front flanks extend at angles β relative to the axially elongated direction, and wherein β>α, and α>45°, and said second portion 14 has a conical surface from which said rings project outwardly.

The body 10 mid-portion has an integrally molded sidewise or transversely extending protrusion 38 defining a finger controllable air inlet 39 in communication with the side port 22. The body wall at 10a has substantially increased thickness outwardly from bore extent 23a at the body mid portion. This establishes a non flexible anchor region for manual gripping, which the body first portion 11 remain sidewise flexible to accommodate to the geometry of the anatomy, such as the mouth, being suctioned.

It will be noted that in FIGS. 1 and 2 the inlet 12 faces axially endwise, in the direction indicated by arrow 50.

In the FIGS. 3 and 4 modification, the inlet or inlets 52 face sidewise, i.e. transversely relative to the longitudinally axial extent of the body first portion 11 shown. Each such inlet preferably has elongated length $l_l$ in the longitudinal direction of 11, and has narrowed width $w_l$ along the length $l_l$ wherein $l_l \gg w_l$. The slot configuration of the inlet to the bore, enhances inlet fluid flow access, directionally, to the bore, and suction access to the in-flow, along the bore.

Preferred highly advantageous operative dimension of the rings are as follows:

| Ring | overall diameters (inches) | ring thickness inches | spacing between rings |
|---|---|---|---|
| 60 | ≅.324 | .031 | .069 |
| 61 | ≅.335 | " | " |
| 62 | ≅.350 | " | " |
| 63 | ≅.360 | " | " |
| 64 | ≅.375 | " | " |
| 65 | ≅.375 | " | " |

The annulus 70 on the body acts as a firm step to limit push-on of the connector tubing, at the body mid-portion.

We claim:

1. A mucous suction device, comprising in combination:
    a) a longitudinally elongated, generally tubular, one-piece plastic body,
    b) said body having an axially elongated tapered, first portion extending toward an inlet proximate one end of the body,
    c) said body having an axially elongated second portion extending toward an outlet proximate an opposite end of the body,
    d) radially outwardly extending annular retention rings on said body second portion, said rings having sharp annular peripheries and said rings being axially resiliently flexible and axially spaced apart,
    e) and there being body side porting between said body first and second portions, said side porting being manually controllable to control suction exertion,
    f) the rings having outwardly tapering peripheries which progressively increase in diameter in a direction toward the body side porting,
    g) the body second portion carrying the rings progressively increasing in diameter in said direction, whereby the rings project outwardly from the body side portion to substantially equal extents.

2. The combination of claim 1 wherein the body has a bore extending between said inlet and outlet, said bore having substantially constant diameter along entire body length.

3. The combination of claim 1 wherein said rings are axially flexible at said peripheries for establishing annular seals in response to axial reception of a connector tubing bore onto and over said body second portion.

4. The combination of claim 1 including a connector tubing having a bore received onto and over said body second portion, said bore having interference engagement with at least three of said rings, whereby said three rings are flexed axially at said peripheries thereof to establish annular seals.

5. The combination of claim 3 wherein said body portion and said rings consist of molded plastic material.

6. The combination of claim 1 wherein said rings have front and back flanks, and wherein for each pair of successive rings, the back flank of one ring of the pair is everywhere spaced axially from the front flank of the other ring of the pair whereby each ring is independently axially flexible.

7. The combination of claim 5 wherein said body portions are translucent.

8. The combination of claim 1 wherein said inlet faces axially endwise.

9. The combination of claim 1 wherein said inlet faces sidewise relative to said body elongated second portion.

10. The combination of claim 9 wherein said inlet has elongated length $l_l$ in the length direction of said body elongated first portion, and has narrowed with $w_l$ along said length $l_l$, and wherein $l_l \gg w_l$.

11. The combination of claim 1 wherein the body has a mid-portion between said first and second portions, said side porting located at said body mid-portion, there being a sideward protrusion integral with said mid-portion, said protrusion defining a finger controllable air inlet in communication with said side porting.

12. The combination of claim 1 including a connector tubing having a bore received onto and over said body second portion, said bore having interference engagement with at least three of said rings, whereby said three rings are flexed axially at said peripheries thereof to establish annular seals.

13. The combination of claim 1 wherein said rings have front and back flanks, and wherein for each pair of successive rings, the back flank of one ring of the pair is everywhere spaced axially from the front flank of the other ring of the pair whereby each ring is independently axially flexible.

14. The combination of claim 1 wherein said inlet faces axially endwise.

15. The combination of claim 1 wherein said inlet faces sidewise relative to said body elongated second portion.

16. The combination of claim 15 wherein said inlet has elongated length $l_l$ in the length direction of said body elongated first portion, and has narrowed with $w_l$ along said length $l_l$, and wherein $l_l \gg w_l$.

17. The combination of claim 16 wherein the body has a bore extending between said inlet and outlet, said bore having substantially constant diameter along entire body length.

18. The combination of claim 13 wherein the back flanks extend at angles α relative to the axially elongated direction and the front flanks extend at angles β relative to the axially elongated direction, and wherein β>α, and α>45°, and said second portion has a conical surface from which said rings project outwardly.

* * * * *